April 12, 1949. W. B. CLARKE Plant Pat. 831
LILAC PLANT
Filed June 4, 1947
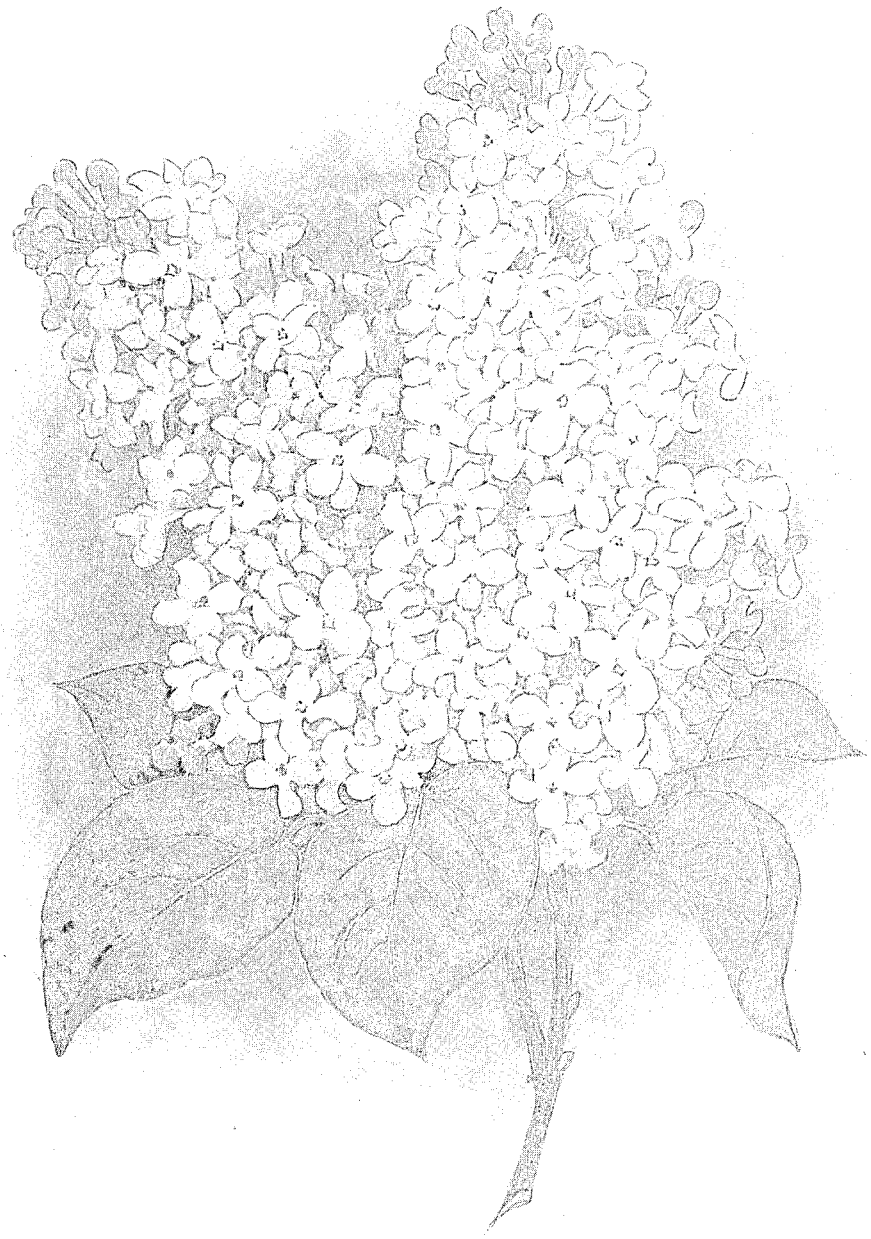
WITNESS
Addison J. Avery
INVENTOR
WALTER BOSWORTH CLARKE,
By Kummer Kummer & Snow,
ATTYS.

Patented Apr. 12, 1949

Plant Pat. 831

UNITED STATES PATENT OFFICE

831

LILAC PLANT

Walter Bosworth Clarke, San Jose, Calif., assignor to W. B. Clarke & Co., San Jose, Calif., a partnership Application June 4, 1947, Serial No. 752,344

1 Claim. (Cl. 47—60)

The present discovery relates to a new and distinct variety of *Syringa vulgaris* or lilac plant, which originated as a cross made by me between unnamed parent plants. This new variety is the result of prolonged breeding efforts to obtain a pure pink variety, carried on by me since 1931. It has been reproduced from buds through several generations and its characteristics appear to be permanently fixed.

Its novelty resides primarily in the unique coloring of the flowers at the different stages of their development, its unusually vigorous growing habit, its heavy production of blooms in the early spring, and the display of stamens in the mouths of the corolla tubes.

Another characteristic of this new variety is the contrast between the dark rose mauve coloring of the buds and the dainty amaranth rose pink of the open flowers.

In general plant structure, this new variety is similar to the well-known *Syringa vulgaris*. The individual floret has the usual, small, bell-shaped, four-toothed calyx, and is approximately ¾ of an inch in width. The panicles are usually compounded, medium in size, pyramidal in shape with the segments spreading and often somewhat reflexed. They are borne terminally. The blooms have a gratifying fragrance.

It blooms profusely in the spring of the year; the first blooms appeared March 31, 1941, at my breeding grounds near San Jose, California. The distinctive characteristics of this plant are evident even while the flower clusters are partly open. Contrast between the buds and the flowers is harmonious. It has a certain delicacy and daintiness that is due to its lack of any coarseness. The stamens show conspicuously in the throats of the open flowers.

The accompanying painting shows the approximate shape of its panicles, and its distinctive coloring.

The color designations according to "A Dictionary of Color by Maerz and Paul" are as follows:

| Item | Plate | Letter | No. |
|---|---|---|---|
| (1) Dominant color of flowers | 49 | G | 1 |
| (2) Throat of corolla | 9 | L | 5 |
| (3) Buds | 41 | I | 6 |
| (4) Leaf | 21 | K | 9 |
| (5) Stem | 15 | C | 3 |

The only other lilac comparable to this new variety is "Esther Staley," shown in my copending application Serial No. 713,862, filed December 4, 1946, now Plant Patent No. 768, issued December 16, 1947. The present plant differs chiefly in its somewhat lighter coloring, its more lax and arching bloom clusters, its stamens showing more vividly in the corolla tube, and its earlier blooming season.

The corolla lobes lie flat and this new variety of lilac presents distinctive masses of amaranth pink color which is made more conspicuous by the dark rosy mauve coloring of the buds. The broad full thyrses on the sturdy stems are outstanding features. It has a sufficient quantity of green foliage to make a pleasing contrast with the lavish display of rich pink coloring.

Having thus disclosed my invention, I claim:

A new and distinct variety of *Syringa vulgaris* or lilac plant, substantially as described, being characterized by the dark rose mauve coloring of its buds and the distinctive amaranth pink of the full-blown flowers, its abundant floriferousness, its vigorous growth, and early blooming habit.

WALTER BOSWORTH CLARKE.

No references cited.